US009907766B2

(12) United States Patent
Kitahara et al.

(10) Patent No.: US 9,907,766 B2
(45) Date of Patent: Mar. 6, 2018

(54) SWEETNESS RECEPTOR ANTAGONIST

(71) Applicant: AJINOMOTO CO., INC., Tokyo (JP)

(72) Inventors: Yoshiro Kitahara, Kawasaki (JP); Koji Ohsumi, Kawasaki (JP); Seiji Kitajima, Kawasaki (JP); Shimpei Ogawa, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 15/389,639

(22) Filed: Dec. 23, 2016

(65) Prior Publication Data

US 2017/0101372 A1    Apr. 13, 2017

Related U.S. Application Data

(63) Continuation of application No. PCT/JP2015/068461, filed on Jun. 26, 2015.

(30) Foreign Application Priority Data

Jun. 27, 2014  (JP) ................ 2014-132466

(51) Int. Cl.
*A61K 31/17* (2006.01)
*C07C 335/20* (2006.01)
*C07C 335/16* (2006.01)

(52) U.S. Cl.
CPC ............ *A61K 31/17* (2013.01); *C07C 335/16* (2013.01); *C07C 335/20* (2013.01)

(58) Field of Classification Search
CPC .................................................. A61K 31/17
USPC ........................................................ 514/524
See application file for complete search history.

(56) References Cited

U.S. PATENT DOCUMENTS

| 2006/0257543 A1 | 11/2006 | Tachdjian et al. |
| 2008/0306093 A1 | 12/2008 | Servant et al. |
| 2014/0004243 A1 | 1/2014 | Tahara et al. |

FOREIGN PATENT DOCUMENTS

| JP | 2008-530017 A | 8/2008 | |
| JP | 2010-531437 A | 9/2010 | |
| WO | WO 2006/084184 A2 | 8/2006 | |
| WO | WO 2006084184 A2 * | 8/2006 | ............. A23L 27/20 |
| WO | WO 2012/121273 A1 | 9/2012 | |

OTHER PUBLICATIONS

Yosuke Masubuchi, et al., "A Novel Regulatory Function of Sweet Taste-Sensing Receptor in Adipogenic Differentiation of 3T3-L1 Cells" Plos One, vol. 8, No. 1, Jan. 15, 2013, pp. 1-12.
Yuko Nakagawa, et al., "Sweet Taste Receptor Expressed in Pancreatic B-Cells Activates the Calcium and Cyclic AMP Signaling Systems and Stimulates Insulin Secretion" Plos One, vol. 4, No. 4, Apr. 8, 2009, pp. 1-10.
Alain Schilling, et al., "Behavioral Study in the Gray Mouse Lemur (*Microcebus murinus*) Using Compounds Considered Sweet by Humans" American Journal of Primatology, vol. 62, 2004, pp. 43-48.
Robert F. Margolskee, et al., "T1R3 and gustducin in gut sense sugars to regulate expression of Na+ -glucose cotransporter 1" PNAS, vol. 104, No. 38, Sep. 18, 2007, pp. 15075-15080.
Yosuke Masubuchi, et al., 'A Novel Regulatory Function of Sweet Taste-Sensing Receptor in Adipogenic Differentiation of 3T3-L1 Cells° Plos One, vol. 8, No. 1, Jan. 15, 2013, pp. 1-12.
Yuko Nakagawa, et al., °Sweet Taste Receptor Expressed in Pancreatic B-Cells Activates the Calcium and Cyclic Amp Signaling Systems and Stimulates Insulin Secretion° Plos One, vol. 4, No. 4, Apr. 8, 2009, pp. 1-10.
George W. Muller, et al., "Carboxylic Acid Replacement Structure-Activity Relationships in Suosan Type Sweeteners. A Sweet Taste Antagonist" Journal of Medicinal Chemistry, vol. 35, 1992, pp. 1747-1751.
Emeline L. Maillet, et al., "Phenoxy Herbicides and Fibrates Potently Inhibit the Human Chemosensory Receptor Subunit T1R3" Journal of Medicinal Chemistry, vol. 52, 2009, pp. 6931-6935.
Becky R. Simon, et al., "Artificial Sweeteners Stimulate Adipogenesis and Suppress Lipolysis Independently of Sweet Taste Receptors" The Journal of Biological Chemistry, vol. 288, No. 45, 2013, pp. 32475-32489.
Alain Schilling, et al., "Behavioral Study in the Gray Mouse Lemur (*Microcebus murinus*) Using Compounds Considered Sweet by Humans" American Journal of Primatology, vol. 62, 2004, pp. 43 48.

\* cited by examiner

*Primary Examiner* — Kathrien Cruz
*Assistant Examiner* — Janet L Coppins
(74) *Attorney, Agent, or Firm* — Oblon, McClelland, Maier & Neustadt, L.L.P.

(57) ABSTRACT

Sweetness receptor antagonists represented by formula (I):

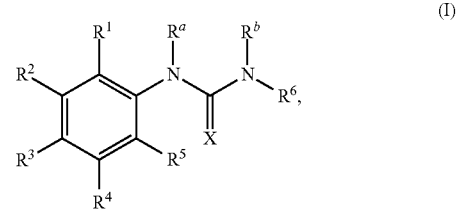

wherein each symbol is described herein, are useful for the prophylaxis or treatment of metabolic syndrome, diabetes, obesity and the like.

17 Claims, No Drawings

SWEETNESS RECEPTOR ANTAGONIST

CROSS REFERENCES TO RELATED APPLICATIONS

This application is a continuation of International Patent Application No. PCT/JP2015/068461, filed on Jun. 26, 2015, and claims priority to Japanese Patent Application No. 2014-132466, filed on Jun. 27, 2014, both of which are incorporated herein by reference in their entireties.

BACKGROUND OF THE INVENTION

Field of the Invention Description

The present invention relates to sweetness receptor antagonists which are useful for the prophylaxis or treatment of metabolic syndrome, diabetes, obesity, and the like.

Discussion of the Background

A sweetness receptor (T1R2/T1R3) is present in oral taste cells, and is known as a receptor to perceive sweetness. In recent years, it has been reported that a sweetness receptor is expressed not only orally but also in the intestine and pancreas (see Proc. Natl. Acad. Sci. USA., 2007, 104, 15075-15080 and PLOS ONE, 2009, volume 4, issue 4, e5106, both of which are incorporated herein by reference in their entireties). A sweetness receptor is also expressed in preadipocyte line 3T3-L1, and is being clarified to be involved in adipogenesis. Therefore, a sweetness receptor antagonist may become a promising target as a therapeutic agent for metabolic syndrome, diabetes, obesity and the like (see PLOS ONE, 2013, volume 8, issue 1, e54500 and Journal of Biological Chemistry, 2013, 288, 32475-32489, both of which are incorporated herein by reference in their entireties).

As sweetness receptor antagonists, inorganic compounds such as zinc sulfate, copper chloride and the like, as well as the organic compounds represented by the following formulae:

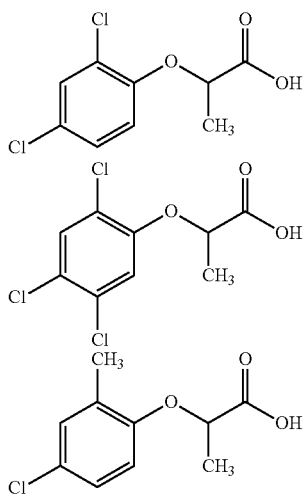

have heretofore been known (see Journal of Medicinal Chemistry, 2009, 52, 6931-6935, which is incorporated herein by reference in its entirety).

On the other hand, American Journal of Primatology, 2004, 62, 43-48, which is incorporated herein by reference in its entirety, describes that a compound represented by the following formula:

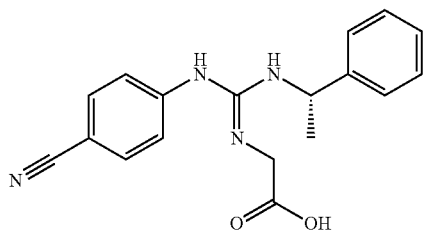 [SMILES: C[C@H](N/C(=N\CC(=O)O)Nc1ccc(C#N)cc1)c1ccccc1]

(SC-45647) has a sweetness receptor agonist activity.

Moreover, WO 2006/084184, which is incorporated herein by reference in its entirety, discloses that a compound represented by the following general formula:

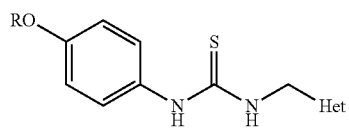

has a sweetness receptor agonist activity.

Furthermore, WO 2012/121273, which is incorporated herein by reference in its entirety, discloses a compound represented by the following general formula (I):

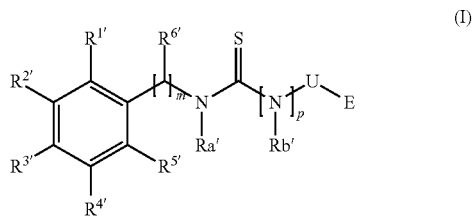

wherein each symbol is as defined in WO 2012/121273, as a saltiness enhancer.

Furthermore, Journal of Medicinal Chemistry, 1992, 35, 1747-1751, which is incorporated herein by reference in its entirety, describes a compound represented by the following formula:

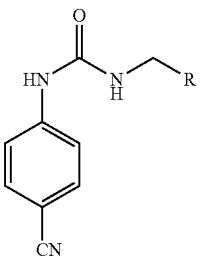

wherein $R=SO_3Na$, as a sweetness antagonist.

However, none of the above-mentioned publications describes or suggests that a compound represented by the following formula (I) of the present invention has a sweetness receptor antagonist activity.

SUMMARY OF THE INVENTION

Accordingly, it is one object of the present invention to provide novel sweetness receptor antagonists.

It is another object of the present invention to provide novel sweetness receptor antagonists which are useful for the prophylaxis or treatment of metabolic syndrome, diabetes, obesity and the like.

It is another object of the present invention to provide novel methods for the prophylaxis or treatment of metabolic syndrome, diabetes, obesity and the like.

These and other objects, which will become apparent during the following detailed description, have been achieved by the inventors' discovery that thiourea compounds having the following structure exhibit a superior sweetness receptor antagonist activity.

Thus, the present invention provides the following:

(1) A sweetness receptor antagonist, comprising a compound represented by formula (I):

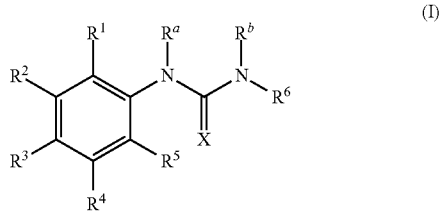

wherein
$R^1$, $R^2$, $R^3$, $R^4$, and $R^5$ are each independently a hydrogen atom or an electron-withdrawing group (provided at least one of $R^1$, $R^2$, $R^3$, $R^4$, and $R^5$ is an electron-withdrawing group);
$R^6$ is an optionally substituted hydrocarbon group or an optionally substituted heterocyclic group;
$R^a$ and $R^b$ are each independently a hydrogen atom or a $C_{1-6}$ alkyl group; and
X is S,
or a salt thereof.

(2) The sweetness receptor antagonist of (1), wherein any one of $R^1$, $R^2$, $R^3$, $R^4$, and $R^5$ is an electron-withdrawing group.

(3) The sweetness receptor antagonist of (2), wherein $R^3$ or $R^4$ is an electron-withdrawing group.

(4) The sweetness receptor antagonist of any of (1)-(3), wherein the electron-withdrawing group is a halogen atom, a halo $C_{1-6}$ alkyl group, or a cyano group.

(5) The sweetness receptor antagonist of any of (1)-(4), wherein $R^6$ is an optionally substituted $C_{1-6}$ alkyl group or an optionally substituted $C_{3-10}$ cycloalkyl group.

(6) The sweetness receptor antagonist of any of (1)-(5), wherein $R^6$ is a $C_{1-6}$ alkyl group, a $C_{3-10}$ cycloalkyl group, a $C_{3-10}$ cycloalkyl-$C_{1-6}$ alkyl group, or a mono- or di-$C_{6-10}$ aryl-$C_{1-6}$ alkyl group.

(7) The sweetness receptor antagonist of any of (1)-(6), wherein both $R^a$ and $R^b$ are hydrogen atoms.

(8) The sweetness receptor antagonist of (1), wherein the compound represented by the formula (I) or a salt thereof is a compound selected from the group consisting of
1-benzyl-3-(3-cyanophenyl)thiourea;
1-benzyl-3-[4-(trifluoromethyl)phenyl]thiourea;
1-benzyl-3-(4-bromophenyl)thiourea;
1-(4-cyanophenyl)-3-cyclooctyl-thiourea;
1-(4-cyanophenyl)-3-cyclohexyl-thiourea;
1-(4-cyanophenyl)-3-(cyclohexylmethyl)thiourea;
1-benzhydryl-3-(4-cyanophenyl)thiourea; and
1-butyl-3-(4-cyanophenyl)thiourea,
or a salt thereof.

(9) An insulin sensitizer, comprising a sweetness receptor antagonist of any of (1)-(8).

(10) A prophylactic and/or therapeutic agent for a disease selected from the group consisting of metabolic syndrome, diabetes and obesity, which comprises a sweetness receptor antagonist of any of (1)-(8).

(11) 1-(4-Cyanophenyl)-3-(cyclohexylmethyl)thiourea or a salt thereof.

Effect of the Invention

According to the present invention, a sweetness receptor antagonist useful for the prophylaxis or treatment of metabolic syndrome, diabetes, obesity and the like can be provided.

DETAILED DESCRIPTION OF THE PREFERRED EMBODIMENTS

The terms used in the present specification are defined below.

In the present specification, the term "halogen atom" means a fluorine atom, a chlorine atom, a bromine atom, or an iodine atom.

In the present specification, examples of the "hydrocarbon group" include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{4-10}$ cycloalkadienyl group, a $C_{6-14}$ aryl group and the like.

In the present specification, the "$C_{1-6}$ alkyl group" is a straight chain or branched alkyl group having 1 to 6 carbon atoms and, for example, a methyl group, an ethyl group, a propyl group, an isopropyl group, a butyl group, an isobutyl group, a sec-butyl group, a tert-butyl group, a pentyl group, a hexyl group and the like can be mentioned.

In the present specification, examples of the "halo $C_{1-6}$ alkyl group" include the aforementioned $C_{1-6}$ alkyl group substituted by 1 to 5 halogen atoms. Specific examples include a fluoromethyl group, a chloromethyl group, a difluoromethyl group, a dichloromethyl group, a trifluoromethyl group, a trichloromethyl group and the like.

In the present specification, the "$C_{2-6}$ alkenyl group" is a straight chain or branched alkenyl group having 2 to 6 carbon atoms and, for example, an ethenyl group, a 1-propenyl group, a 2-propenyl group, a 2-methyl-1-propenyl group, a 1-butenyl group, a 2-butenyl group, a 3-butenyl group, a pentenyl group, a hexenyl group and the like can be mentioned.

In the present specification, the "$C_{2-6}$ alkynyl group" is a straight chain or branched alkynyl group having 2 to 6 carbon atoms and, for example, an ethynyl group, a 1-propynyl group, a 2-propynyl group, a 1-butynyl group, a 2-butynyl group, a 3-butynyl group, a pentynyl group, a hexynyl group and the like can be mentioned.

In the present specification, examples of the "$C_{3-10}$ cycloalkyl group" include a cyclopropyl group, a cyclobutyl group, a cyclopentyl group, a cyclohexyl group, a cycloheptyl group, a cyclooctyl group and the like.

In the present specification, examples of the "$C_{3-10}$ cycloalkenyl group" include a cyclopropenyl group, a cyclobutenyl group, a cyclopentenyl group, a cyclohexenyl group, a cycloheptenyl group, a cyclooctenyl group and the like.

In the present specification, examples of the "$C_{4-10}$ cycloalkadienyl group" include a cyclobutadienyl group, a cyclopentadienyl group, a cyclohexadienyl group, a cycloheptadienyl group, a cyclooctadienyl group and the like.

In the present specification, examples of the "$C_{6-10}$ aryl group" include a phenyl group, a naphthyl group and the like.

In the present specification, examples of the "$C_{3-10}$ cycloalkyl-$C_{1-6}$ alkyl group" include a cyclohexylmethyl group, a cyclobutylmethyl group, a cyclopentylmethyl group, a cyclohexylmethyl group, a cycloheptylmethyl group, a cyclooctylmethyl group and the like.

In the present specification, examples of the "mono- or di-$C_{6-10}$ aryl-$C_{1-6}$ alkyl group" include a benzyl group, a phenethyl group, a naphthylmethyl group, a diphenylmethyl group and the like.

In the present specification, examples of the "$C_{1-6}$ alkyl-carbonyl group" include a methylcarbonyl group, an ethylcarbonyl group, a propylcarbonyl group, an isopropylcarbonyl group, a butylcarbonyl group, an isobutylcarbonyl group, a sec-butylcarbonyl group, a tert-butylcarbonyl group and the like.

In the present specification, examples of the "$C_{1-6}$ alkoxycarbonyl group" include a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group and the like.

In the present specification, examples of the "$C_{1-6}$ alkylsulfonyl group" include a methylsulfonyl group, an ethylsulfonyl group, a propylsulfonyl group, an isopropylsulfonyl group, a butylsulfonyl group, an isobutylsulfonyl group, a sec-butylsulfonyl group, a tert-butylsulfonyl group and the like.

In the present specification, examples of the "heterocyclic group" include an aromatic heterocyclic group, a nonaromatic heterocyclic group and the like, each containing, as a ring-constituting atom besides carbon atom, 1 to 4 hetero atoms selected from nitrogen atom, sulfur atom and oxygen atom.

In the present specification, examples of the "aromatic heterocyclic group" include a 5- to 14-membered (preferably 5- to 10-membered) aromatic heterocyclic group containing, as a ring-constituting atom besides carbon atom, 1 to 4 hetero atoms selected from nitrogen atom, sulfur atom and oxygen atom.

Preferable examples of the "aromatic heterocyclic group" include monocyclic aromatic heterocyclic groups such as thienyl group, furyl group, pyrrolyl group, imidazolyl group, pyrazolyl group, thiazolyl group, isothiazolyl group, oxazolyl group, isoxazolyl group, pyridyl group, pyrazinyl group, pyrimidinyl group, pyridazinyl group, oxadiazolyl group, triazolyl group, tetrazolyl group, triazinyl group and the like; and fused polycyclic aromatic heterocyclic groups such as benzothiophenyl group, benzofuranyl group, benzimidazolyl group, benzoxazolyl group, benzoisooxazolyl group, benzothiazolyl group, benzoisothiazolyl group, benzotriazolyl group, imidazopyridinyl group, thienopyridinyl group, furopyridinyl group, pyrrolopyridinyl group, pyrazolopyridinyl group, oxazolopyridinyl group, thiazolopyridinyl group, imidazopyrazinyl group, imidazopyrimidinyl group, thienopyrimidinyl group, furopyrimidinyl group, pyrrolopyrimidinyl group, pyrazolopyrimidinyl group, oxazolopyrimidinyl group, thiazolopyrimidinyl group, pyrazolotriazinyl group, indolyl group, isoindolyl group, purinyl group, isoquinolyl group, quinolyl group, phthalazinyl group, naphthyridinyl group, quinoxalinyl group, quinazolinyl group, cinnolinyl group and the like.

In the present specification, examples of the "nonaromatic heterocyclic group" include a 3- to 14-membered (preferably 3 to 10-membered) nonaromatic heterocyclic group containing, as a ring-constituting atom besides carbon atom, 1 to 4 hetero atoms selected from nitrogen atom, sulfur atom and oxygen atom.

Preferable examples of the "nonaromatic heterocyclic group" include monocyclic nonaromatic heterocyclic groups such as aziridinyl group, oxiranyl group, thiiranyl group, an azetidinyl group, an oxetanyl group, thietanyl group, tetrahydrothienyl group, tetrahydrofuranyl group, pyrrolinyl group, pyrrolidinyl group, imidazolinyl group, imidazolidinyl group, oxazolinyl group, oxazolidinyl group, pyrazolinyl group, pyrazolidinyl group, thiazolinyl group, thiazolidinyl group, tetrahydroisothiazolyl group, tetrahydrooxazolyl group, tetrahydroisooxazolyl group, piperidinyl group, piperazinyl group, tetrahydropyridinyl group, dihydropyridinyl group, dihydrothiopyranyl group, tetrahydropyrimidinyl group, tetrahydropyridazinyl group, dihydropyranyl group, tetrahydropyranyl group, tetrahydrothiopyranyl group, morpholinyl group, thiomorpholinyl group, azepanyl group, diazepanyl group, azepinyl group, oxepanyl group, azocanyl group, diazocanyl group and the like; and fused polycyclic nonaromatic heterocyclic groups such as dihydrobenzofuranyl group, dihydrobenzoimidazolyl group, dihydrobenzooxazolyl group, dihydrobenzothiazolyl group, dihydrobenzoisothiazolyl group, tetrahydroisoquinolyl group, tetrahydroquinolyl group, indolinyl group, isoindolinyl group, tetrahydrobenzoazepinyl group, tetrahydroquinoxalinyl group, tetrahydrophthalazinyl group, tetrahydronaphthyridinyl group, tetrahydroquinazolinyl group, tetrahydrocinnolinyl group and the like.

In the present specification, examples of the substituent in the case of "optionally substituted" include
  (1) a halogen atom,
  (2) a cyano group,
  (3) a nitro group,
  (4) an oxo group,
  (5) a hydroxy group,
  (6) a $C_{1-6}$ alkyl group,
  (7) a $C_{2-6}$ alkenyl group,
  (8) a $C_{2-6}$ alkynyl group,
  (9) a $C_{3-10}$ cycloalkyl group,
  (10) a $C_{3-10}$ cycloalkenyl group,
  (11) a $C_{6-14}$ aryl group,
  (12) a $C_{1-6}$ alkoxy group,
  (13) a $C_{6-14}$ aryloxy group,
  (14) a 5- to 14-membered aromatic heterocyclyloxy group,
  (15) a 3- to 14-membered non-aromatic heterocyclyloxy group,
  (16) a $C_{1-6}$ alkylthio group,
  (17) a $C_{6-14}$ arylthio group,
  (18) a 5- to 14-membered aromatic heterocyclylthio group,
  (19) a 3- to 14-membered non-aromatic heterocyclylthio group,
  (20) a 5- to 14-membered aromatic heterocyclic group,
  (21) a 3- to 14-membered nonaromatic heterocyclic group,
  (22) a $C_{1-6}$ alkyl-carbonyl group,
  (23) a $C_{6-14}$ aryl-carbonyl group,
  (24) a 5- to 14-membered aromatic heterocyclylcarbonyl group,
  (25) a 3- to 14-membered non-aromatic heterocyclylcarbonyl group,
  (26) a carboxy group,
  (27) a $C_{1-6}$ alkoxy-carbonyl group,
  (28) a $C_{6-14}$ aryloxy-carbonyl group,
  (29) a carbamoyl group,

(30) a thiocarbamoyl group,
(31) a mono- or di-$C_{1-6}$ alkyl-carbamoyl group,
(32) a mono- or di-$C_{1-6}$ alkyl-thiocarbamoyl group,
(33) a $C_{1-6}$ alkylsulfonyl group,
(34) a $C_{6-14}$ arylsulfonyl group,
(35) an amino group,
(36) a mono- or di-$C_{1-6}$ alkylamino group,
(37) a $C_{1-6}$ alkyl-carbonylamino group,
(38) a $C_{6-14}$ aryl-carbonylamino group,
(39) a $C_{1-6}$ alkylsulfonylamino group,
(40) a $C_{6-14}$ arylsulfonylamino group and the like.

The number of the above-mentioned substituents in the case of "optionally substituted" is, for example, 1 to 5, preferably 1 to 3. When the number of the substituents is two or more, the respective substituents may be the same or different.

Each substituent in the formula (I) is explained below.

$R^1$, $R^2$, $R^3$, $R^4$ and $R^5$ are each independently a hydrogen atom or an electron-withdrawing group (provided at least one of $R^1$, $R^2$, $R^3$, $R^4$ and $R^5$ is an electron-withdrawing group).

In a preferable embodiment, any one of $R^1$, $R^2$, $R^3$, $R^4$, and $R^5$ is an electron-withdrawing group.

In a more preferable embodiment, $R^3$ or $R^4$ is an electron-withdrawing group. That is, 1) $R^1$, $R^2$, $R^4$, and $R^5$ are hydrogen atoms, and $R^3$ is an electron-withdrawing group, or 2) $R^1$, $R^2$, $R^3$, and $R^5$ are hydrogen atoms, and $R^4$ is an electron-withdrawing group.

The electron-withdrawing group for $R^1$, $R^2$, $R^3$, $R^4$, or $R^5$ is not particularly limited as long as it is a group having a property of withdrawing an electron from a benzene ring bonded thereto and, for example, a halogen atom, a halo $C_{1-6}$ alkyl group, a cyano group, a nitro group, a $C_{1-6}$ alkyl-carbonyl group, a $C_{1-6}$ alkoxy-carbonyl group, a carboxy group, a $C_{1-6}$ alkylsulfonyl group and the like can be mentioned. Preferred are a halogen atom (e.g., bromine atom), a halo $C_{1-6}$ alkyl group (e.g., trifluoromethyl group), and a cyano group.

$R^6$ is an optionally substituted hydrocarbon group or an optionally substituted heterocyclic group.

$R^6$ is preferably an optionally substituted hydrocarbon group.

$R^6$ is more preferably an optionally substituted $C_{1-6}$ alkyl group or an optionally substituted $C_{3-10}$ cycloalkyl group.

$R^6$ is further preferably a $C_{1-6}$ alkyl group (e.g., a butyl group), a $C_{3-10}$ cycloalkyl group (e.g., cyclohexyl group, cycloheptyl group, cyclooctyl group), a $C_{3-10}$ cycloalkyl-$C_{1-6}$ alkyl group (e.g., cyclohexylmethyl group) or a mono- or di-$C_{6-10}$ aryl-$C_{1-6}$ alkyl group (e.g., benzyl group, diphenylmethyl group).

$R^a$ and $R^b$ are each independently a hydrogen atom or a $C_{1-6}$ alkyl group.

Preferably, both $R^a$ and $R^b$ are hydrogen atoms.

X is S.

As a compound represented by formula (I), a compound wherein
1) $R^1$, $R^2$, $R^4$, and $R^5$ are hydrogen atoms, and $R^3$ is an electron-withdrawing group, or 2) $R^1$, $R^2$, $R^3$, and $R^5$ are hydrogen atoms, and $R^4$ is an electron-withdrawing group;
$R^6$ is an optionally substituted $C_{1-6}$ alkyl group or an optionally substituted $C_{3-10}$ cycloalkyl group;
both $R^a$ and $R^b$ are hydrogen atoms; and
X is S
is preferable.

As a compound represented by formula (I), a compound wherein
1) $R^1$, $R^2$, $R^4$, and $R^5$ are hydrogen atoms, and $R^3$ is a halogen atom (e.g., bromine atom), a halo $C_{1-6}$ alkyl group (e.g., trifluoromethyl group) or a cyano group, or 2) $R^1$, $R^2$, $R^3$, and $R^5$ are hydrogen atoms, and $R^4$ is a halogen atom (e.g., bromine atom), a halo $C_{1-6}$ alkyl group (e.g., trifluoromethyl group) or a cyano group;
$R^6$ is a $C_{1-6}$ alkyl group (e.g., a butyl group), a $C_{3-10}$ cycloalkyl group (e.g., cyclohexyl group, cycloheptyl group, cyclooctyl group), a $C_{3-10}$ cycloalkyl-$C_{1-6}$ alkyl group (e.g., cyclohexylmethyl group) or a mono- or di-$C_{6-10}$ aryl-$C_{1-6}$ alkyl group (e.g., benzyl group, diphenylmethyl group);
both $R^a$ and $R^b$ are hydrogen atoms; and
X is S
is more preferable.

Specific examples of a compound represented by formula (I) include the compounds recited in the following Examples, and the compounds of Examples 1 to 8 are preferable.

Examples of the salts of a compound represented by formula (I) include salts with inorganic acids, salts with organic acids, salts with inorganic bases, salts with organic bases, salts with acidic or basic amino acids and the like.

Examples of the salts with inorganic acids include hydrochloride, hydrobromide, sulfate, nitrate, phosphate salts, and the like.

Examples of the salts with organic acids include formate, acetate, trifluoroacetate, oxalate, succinate, maleate, fumarate, citrate, tartrate, methanesulfonate, ethanesulfonate, benzenesulfonate, p-toluenesulfonate salts, and the like.

Examples of the salts with inorganic bases include sodium salts, potassium salts, calcium salts, magnesium salts, ammonium salts, and the like.

Examples of the salts with organic bases include salts with methylamine, diethylamine, trimethylamine, triethylamine, ethanolamine, diethanolamine, triethanolamine, ethylenediamine, tris(hydroxymethyl)methylamine, dicyclohexylamine, N,N'-dibenzylethylenediamine, guanidine, pyridine, picoline, choline, cinchonine, meglumine, and the like.

Examples of the salts with acidic or basic amino acids include salts with aspartic acid, glutamic acid, arginine, lysine, and ornithine.

When a compound represented by formula (I) or a salt thereof (hereinafter sometimes to be abbreviated as compound (I)) has an isomer such as optical isomer, stereoisomer, regioisomer, rotamer and the like, any one of the isomers and mixtures thereof are also encompassed in the compound of the present invention. For example, when the compound of the present invention contains an optical isomer, an optical isomer resolved from the racemate is also encompassed in the compound of the present invention. These isomers can be each obtained as a single product by a synthesis method known per se, a separation method (e.g., concentration, solvent extraction, column chromatography, recrystallization, etc.), an optical resolution method (e.g., fractional recrystallization method, chiral column method, diastereomer method) and the like.

Since the compound (I) of the present invention has a superior sweetness receptor antagonist activity, it can be used as a medicament such as a sweetness receptor antagonist, an insulin sensitizer, or a prophylactic or therapeutic agent for metabolic syndrome, diabetes, obesity and the like, and can be directly administered or administered as a pharmaceutical composition mixed with a pharmaceutically acceptable carrier according to a method known per se, to a mammal (e.g., human, monkey, bovine, horse, mouse, rat etc.) orally or parenterally (e.g., intravenously, subcutaneous, intramuscular, suppository, intestinal infusion, ointment, patch, sublingual, instillation, inhalation etc.). While the dose employed for the above-mentioned object is determined according to the desired treatment effect, administration method, treatment period, age, body weight and the like, a general daily dose for an adult by an oral or parenteral route is 1 μg to 10 g by oral administration, and 0.01 μg to 1 g by parenteral administration, which is administered in one to several portions per day. The content of compound (I) of the present invention in the above-mentioned pharmaceutical composition is about 0.01 wt % to 100 wt % of the whole composition.

As a pharmaceutically acceptable carrier in the pharmaceutical composition of the present invention, various organic or inorganic carrier substances conventionally used as preparation materials can be mentioned and, for example, excipients, lubricants, binders, disintegrants, water-soluble polymers, basic inorganic salts for solid preparations; and solvents, solubilizing agents, suspending agents, isotonicity agents, buffering agents, soothing agents and the like for liquid preparations can be mentioned. When necessary, conventional additives such as preservatives, antioxidants, colorants, sweetening agents, souring agents, foaming agents, flavors, and the like can also be used.

Examples of the dosage form of such pharmaceutical composition include tablet, powder, pill, granule, capsule, suppository, liquid, sugar coating agent, depot, syrup, suspension, emulsion, troche, hypoglottis, adhesive preparation, orally disintegrant (tablet), inhalant, enteroclysis, ointment, adhesive preparation, tape and eye drop.

The pharmaceutical composition of the present invention can be produced by a method conventionally used in the technical field of formulation preparation, for example, the method described in the Japanese Pharmacopoeia, which is incorporated herein by reference in its entirety, and the like. Specific production methods of preparation are described in detail in the following.

For example, when the compound (I) of the present invention is formulated as an oral preparation, an excipient and, where necessary, binder, disintegrant, lubricant, colorant, flavoring agent and the like are added, and the mixture is formulated into, for example, tablet, powder, pill, granule, capsule, solution, sugar coating agent, depot, syrup and the like by a conventional method. As the excipient, lactose, cornstarch, sucrose, glucose, sorbit, crystalline cellulose and the like are used; as the binder, poly(vinyl alcohol), polyvinyl ether, ethylcellulose, methylcellulose, gum arabic, tragacanth, gelatin, shellac, hydroxypropylcellulose, hydroxypropylstarch, polyvinylpyrrolidone and the like are used; as the disintegrant, starch, agar, gelatin powder, crystalline cellulose, calcium carbonate, sodium hydrogen carbonate, calcium citrate, dextran, pectin and the like are used; as the lubricant, magnesium stearate, talc, polyethylene glycol, silica, hydrogenated vegetable oil and the like are used; as the colorant, those permitted to be added to pharmaceutical products are used; and as the flavoring agent, cocoa powder, menthol, aromatic acid, peppermint oil, borneol, cinnamon powder and the like are used. These tablets and granules may be appropriately applied with sugar coating, gelatin coating, or other coating as necessary.

When an injection is to be prepared, a pH adjuster, buffering agent, stabilizer, preservative and the like are added as necessary, and subcutaneous, intramuscular, intravenous injections are produced by a conventional method.

As mentioned above, the compound (I) of the present invention can be used singly as an insulin sensitizer, or a prophylactic or therapeutic agent for metabolic syndrome, diabetes or obesity. It can also be used in combination with other generally-used therapeutic agents for diabetes, or a prophylactic or therapeutic agent for diabetic complications. Examples of generally-used therapeutic agents for diabetes, and a prophylactic or therapeutic agent for diabetic complications include one kind of insulin preparation, insulin derivative, insulin-like agonist, insulin secretagogue, insulin sensitizer, biguanide, gluconeogenesis inhibitor, sugar absorption inhibitor, renal glucose reabsorption inhibitor, β3 adrenoceptor agonist, glucagon-like peptide-1 (7-37), glucagon-like peptide-1 (7-37) analogs, glucagon-like peptide-1 receptor agonist, dipeptidyl peptidase IV inhibitor, aldose reductase inhibitors, glycation end product inhibitor, glycogen synthase kinase-3 inhibitor, glycogen phosphorylase inhibitor, hypolipidemic drug, anorexiant, lipase inhibitor, antihypertensive agent, peripheral circulation improving drug, antioxidant, therapeutic drug for diabetic neuropathy and the like, and combinations and mixtures of two or more kinds thereof.

A medicament to be used in combination with the compound (I) of the present invention may be mixed to give a single agent, or each is separately formulated as a preparation, or a combination preparation (set, kit, pack) containing each separately-formulated preparation in one container may be afforded.

The administration form for combined use is not particularly limited and, for example, (1) administration of a single preparation, (2) simultaneous administration of separate preparations by the same administration route, (3) administration of separate preparations by the same administration route in a staggered manner, (4) simultaneous administration of separate preparations by different administration routes, (5) administration of separate preparations by different administration routes in a staggered manner and the like can be mentioned.

The production method of compound (I) is not particularly limited, and compound (I) can be produced by a combination of known methods. Specifically, it can be synthesized by the following method, to which the production method is not limited.

In compound (I), a compound wherein $R^a$ is a hydrogen atom (hereinafter to be referred to as compound (I-a)) and a compound wherein $R^b$ is a hydrogen atom (hereinafter to be referred to as compound (I-b)) can be produced by the following production methods.

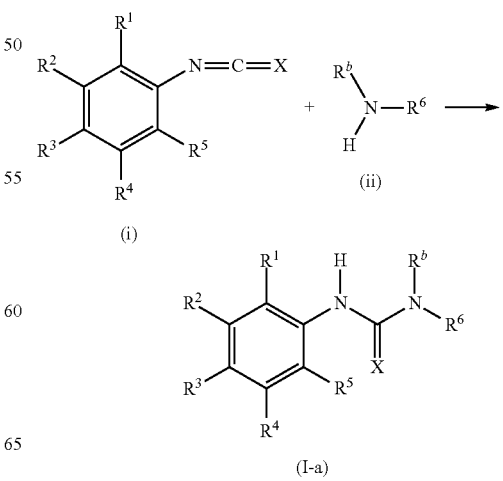

-continued

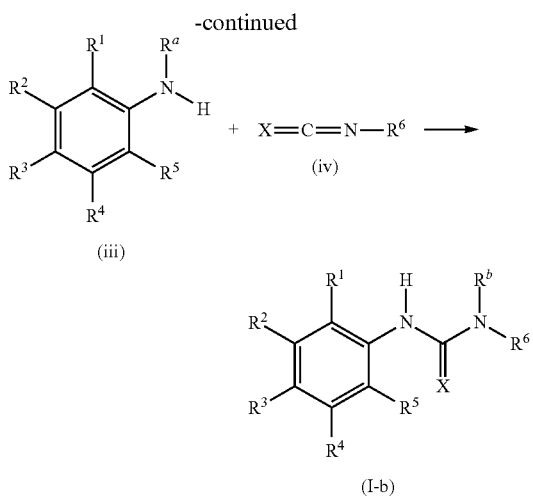

wherein each symbol is as defined above.

Compound (I-a) can be produced by reacting isothiocyanate (i) with amine (ii), and compound (I-b) can be produced by reacting amine (iii) with isothiocyanate (iv). The amount of isothiocyanate (i) or (iv) to be used is 0.7 to 2.0 equivalents, preferably 0.8 to 1.2 equivalents, relative to amine (ii) or (iii), respectively.

This reaction may be performed in the presence of a base such as triethylamine, sodium hydroxide, potassium hydroxide, N-methylmorpholine, N-methylpiperidine, N,N-diisopropylethylamine and the like. The amount of the base to be used is 1.0 to 5.0 equivalents, preferably 2.0 to 3.0 equivalents, relative to amine (ii) or (iii).

As the solvent to be used, tetrahydrofuran, dioxane, dichloromethane, chloroform, N,N-dimethylformamide, dimethyl sulfoxide, N-methylpyrrolidone, a mixed solvent thereof, a mixed solvent of these and water and the like can be used. The amount of the solvent to be used is 1- to 100-fold weight, preferably 10- to 30-fold weight, relative to amine (ii) or (iii).

The reaction time is 1 to 50 hr, preferably 3 to 24 hr.
The reaction temperature is 0 to 80° C., preferably 5 to 60° C.

Compound (I) wherein either $R^a$ or $R^b$ is a $C_{1-6}$ alkyl group, or both $R^a$ and $R^b$ are $C_{1-6}$ alkyl groups can be produced by reacting compound (I-a) or compound (I-b) with an alkylating agent such as halogenated $C_{1-6}$ alkyl (e.g., methyl iodide, ethyl iodide) and the like in the presence of a base such as sodium hydride, potassium hydride, n-butyllithium, t-butyllithium and the like according to a known method.

In each of the aforementioned reactions, when a starting compound has an amino group, a carboxy group, a hydroxy group or a carbonyl group as a substituent, a protecting group generally used in the peptide chemistry and the like may be introduced into these groups, and the object compound can be obtained by removing the protecting group after the reaction as necessary.

The above-mentioned protecting group can be removed by a known method, for example, the method described in Protective Groups in Organic Synthesis, John Wiley and Sons (1980), which is incorporated herein by reference in its entirety, and the like.

Compound (I) obtained by the aforementioned each reaction can be isolated and purified by a conventional method. For purification by crystallization, for example, ethyl acetate, ethanol, methanol, diethyl ether, chloroform, dichloromethane, hexane and a mixed solvent thereof can be used as the solvent. For purification by chromatography, preparative thin layer chromatography or silica gel column chromatography can be used. As the eluent therefor, the solvents recited earlier as the solvent for crystallization can be used.

Other features of the invention will become apparent in the course of the following descriptions of exemplary embodiments which are given for illustration of the invention and are not intended to be limiting thereof.

EXAMPLES

Example 4: Synthesis of
1-(4-cyanophenyl)-3-cyclooctyl-thiourea

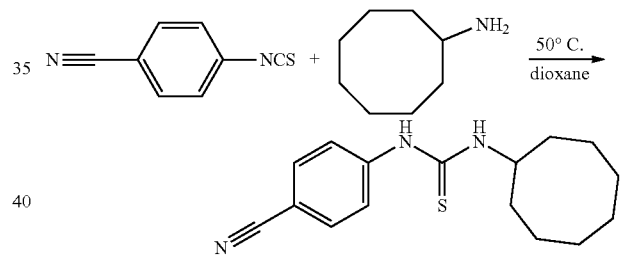

To 4-cyanobenzoisothiocyanate (1.0 g, 6.3 mmol) and cyclooctanamine (0.94 mL, 6.3 mmol) was added dioxane (20 mL) and the mixture was stirred at 50° C. for 15 hours. After confirmation of the completion of the reaction, the reaction mixture was concentrated. The residue was crystallized from ethyl acetate-hexane to give the title compound (1.8 g) (quantitative).

Example compounds synthesized according to the method described in Example 4 and Reference Example compounds are shown in the following Tables 1-1 and 1-2.

TABLE 1-1

| compound No. | structural formula | MASS (ESI) | $^1$H-NMR (300 MHz, CDCl$_3$) | compound name (IUPAC) |
|---|---|---|---|---|
| Example 1 | 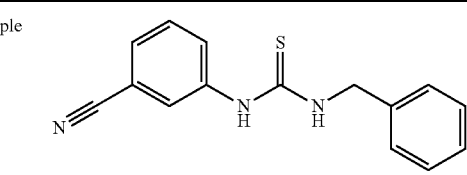 | 268 (M + H)+ | δ 7.96 (1H, brs), 7.48-7.53 (4H, m), 7.29-7.38 (5H, m), 6.30 (1H, brs), 4.85 (2H, d, J = 3.8 Hz) | 1-benzyl-3-(3-cyanophenyl)thiourea |

TABLE 1-1-continued

| compound No. | structural formula | MASS (ESI) | ¹H-NMR (300 MHz, CDCl$_3$) | compound name (IUPAC) |
|---|---|---|---|---|
| Example 2 | | 311 (M + H)+ | δ 7.99 (1H, brs), 7.64 (2H, d, J = 6.3 Hz), 7.29-7.38 (7H, m), 6.35 (1H, brs), 4.87 (2H, d, J = 4.2 Hz) | 1-benzyl-3-[4-(trifluoromethyl)phenyl]thiourea |
| Example 3 | | 322 (M + H)+ | δ 7.78 (1H, brs), 7.52 (2H, d, J = 7.2 Hz), 7.26-7.34 (5H, m), 7.09 (2H, d, J = 7.2 Hz), 6.17 (1H, brs), 4.85 (2H, d, J = 4.2 Hz) | 1-benzyl-3-(4-bromophenyl)thiourea |
| Example 4 | | 288 (M + H)+ | δ 8.04 (1H, brs), 7.68 (2H, d, J = 6.6 Hz), 7.32 (2H, d, J = 6.0 Hz), 6.18 (1H, brd, J = 5.1 Hz), 4.42-4.55 (1H, m), 1.90-2.02 (2H, m), 1.50-1.70 (12H, m) | 1-(4-cyanophenyl)-3-cyclooctyl-thiourea |
| Example 5 | | 260 (M + H)+ | δ 7.98 (1H, brs), 7.69 (2H, d, J = 6.3 Hz), 7.32 (2H, d, J = 6.3 Hz), 6.08 (1H, brs), 4.24, 1H, brs), 2.05-2.15 (2H, m), 1.58-1.78 (4H, m), 1.36-1.50 (2H, m), 1.12-1.30 (3H, m) | 1-(4-cyanophenyl)-3-cyclohexyl-thiourea |
| Example 6 | | 274 (M + H)+ | δ 7.94 (1H, brs), 7.70 (2H, d, J = 5.1 Hz), 7.35 (2H, brs), 6.26 (1H, brs), 3.49 (2H, brs), 1.50-1.80 (8H, m), 1.10-1.32 (3H, m), 0.92-1.05 (2H, m) | 1-(4-cyanophenyl)-3-cyclohexylmethyl)thiourea |

TABLE 1-2

| compound No. | structural formula | MASS (ESI) | ¹H-NMR (300 MHz, CDCl$_3$) | compound name (IUPAC) |
|---|---|---|---|---|
| Example 7 | | 344 (M + H)+ | δ 7.70-7.90 (1H, m), 7.61 (2H, d, J = 6.3 Hz), 7.22-7.40 (13H, m), 6.74 (1H, brd, J = 4.5 Hz) | 1-benzhydryl-3-(4-cyanophenyl)thiourea |
| Example 8 | | 234 (M + H)+ | δ 8.15 (1H, brs), 7.68 (2H, d, J = 5.1 Hz), 7.34 (2H, brd, J = 5.7 Hz), 6.23 (1H, brs), 3.63-3.70 (2H, m), 1.58-1.65 (2H, m), 1.35-1.40 (2H, m), 0.95 (3H, t, J = 5.4 Hz) | 1-butyl-3-(4-cyanophenyl)thiourea |

TABLE 1-2-continued

| compound No. | structural formula | MASS (ESI) | $^1$H-NMR (300 MHz, CDCl$_3$) | compound name (IUPAC) |
|---|---|---|---|---|
| Example 9 | 4-cyanophenyl-NH-C(=S)-NH-CH2-phenyl | 268 (M + H)+ | δ 10.0 (1H, brs), 8.55 (1H, brs), 7.38-7.79 (4H, m), 7.32-7.38 (4H, m), 7.25-7.32 (1H, m), 4.75 (2H, s) | 1-benzyl-3-(4-cyanophenyl)thiourea |
| Ref. Example 1 | 4-cyanophenyl-NH-C(=O)-NH-CH2-phenyl | 252 (M + H)+ | δ 7.45 (2H, d, J = 6.7 Hz), 7.35 (2H, d, J = 6.7 Hz), 7.28-7.34 (5H, m), 6.63 (1H, brs), 5.07 (1H, brs), 4.44 (2H, d, J = 4.2 Hz) | 1-benzyl-3-(4-cyanophenyl)urea |
| Example 10 | 4-cyanophenyl-NH-C(=S)-NH-cycloheptyl | 274 (M + H)+ | δ 8.05 (1H, brs), 7.67 (2H, d, J = 6.6 Hz), 7.32 (2H, d, J = 6.3 Hz), 6.16 (1H, brd, J = 4.8 Hz), 4.35-4.50 (1H, m), 2.05-2.15 (2H, m), 1.45-1.70 (10H, m) | 1-(4-cyanophenyl)-3-cycloheptyl-thiourea |

Experimental Example 1: Evaluation of Sweetness Receptor Antagonist Action by Using Preadipocyte Line (3T3-L1)

3T3-L1 was seeded in a collagen-coated 96 well plate at $0.7 \times 10^5$ cells/well and cultured overnight in a medium containing 10% bovine serum (dulbecco's modified eagle's medium) in an incubator at 37° C., 5% CO$_2$. After 26 hours from the start of the culture, calcium sensitive dye (Calcium 5, Calcium assay kit Express, Molecular Device) diluted 80-fold with Assay buffer (20 mM HEPES, 146 mM NaCl, 1 mM MgSO$_4$, 1.39 mM glucose, 1 mM CaCl$_2$, 2.5 mM Probenecid, 0.1% Bovine serum albumin) was added to allow for intracellular intake, and a test compound diluted with Assay buffer (8-series dilution from 50 μM) was added. After 15 minutes from the addition of the test compound, 2 mM acesulfame potassium (AceK) Assay buffer solution was added as a sweetness receptor agonist, and changes in the concentration of calcium in the cell were measured. A 50% inhibitory concentration (IC50 value) was calculated from the obtained calcium concentration profile curve. The results are shown in Table 2.

TABLE 2

| compound No. | structural formula | 3T3-L1 IC50(uM) |
|---|---|---|
| Example 1 | 3-cyanophenyl-NH-C(=S)-NH-CH2-phenyl | 4.0 |
| Example 2 | 4-(trifluoromethyl)phenyl-NH-C(=S)-NH-CH2-phenyl | 2.3 |
| Example 3 | 4-bromophenyl-NH-C(=S)-NH-CH2-phenyl | 6.6 |

TABLE 2-continued

| compound No. | structural formula | 3T3-L1 IC50(uM) |
|---|---|---|
| Example 4 | 4-cyanophenyl-NH-C(=S)-NH-cyclooctyl | 1.3 |
| Example 5 | 4-cyanophenyl-NH-C(=S)-NH-cyclohexyl | 3.4 |
| Example 6 | 4-cyanophenyl-NH-C(=S)-NH-CH2-cyclohexyl | 1.8 |
| Example 7 | 4-cyanophenyl-NH-C(=S)-NH-CH(phenyl)2 | 2.2 |
| Example 8 | 4-cyanophenyl-NH-C(=S)-NH-butyl | 1.4 |
| Example 9 | 4-cyanophenyl-NH-C(=S)-NH-CH2-phenyl | 12.8 |
| Ref. Example 1 | 4-cyanophenyl-NH-C(=O)-NH-CH2-phenyl | 16.6 |
| Example 10 | 4-cyanophenyl-NH-C(=S)-NH-cycloheptyl | 12.5 |

TABLE 2-continued

| compound No. | structural formula | 3T3-L1 IC50(uM) |
|---|---|---|
| 2,4-DP | | >100 |

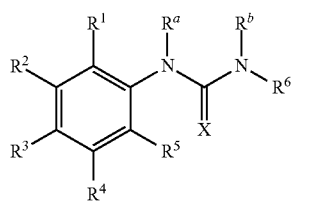

The compound of the present invention strongly inhibited the sweetness receptor agonist action of acesulfame potassium (AceK).

INDUSTRIAL APPLICABILITY

The present invention can provide a sweetness receptor antagonist useful for the prophylaxis or treatment of metabolic syndrome, diabetes, obesity and the like.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. 1-(4-Cyanophenyl)-3-(cyclohexylmethyl)thiourea or a salt thereof.

2. A method for the treatment of a disease selected from the group consisting of metabolic syndrome, diabetes, and obesity, which comprises administering to a subject in need thereof a compound represented by formula (I):

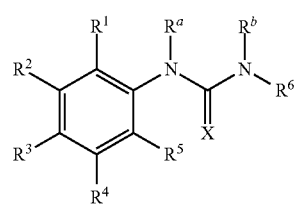

wherein
$R^1$, $R^2$, $R^3$, $R^4$, and $R^5$ are each independently a hydrogen atom or an electron-withdrawing group, provided at least one of $R^1$, $R^2$, $R^3$, $R^4$, and $R^5$ is an electron-withdrawing group;
$R^6$ is an optionally substituted hydrocarbon group or an optionally substituted heterocyclic group;
$R^a$ and $R^b$ are each independently a hydrogen atom or a $C_{1-6}$ alkyl group; and
X is S,
or a salt thereof.

3. The method according to claim 2, wherein any one of $R^1$, $R^2$, $R^3$, $R^4$, and $R^5$ is an electron-withdrawing group.

4. The method according to claim 3, wherein $R^3$ or $R^4$ is an electron-withdrawing group.

5. The method according to claim 2, wherein said electron-withdrawing group is a halogen atom, a halo $C_{1-6}$ alkyl group, or a cyano group.

6. The method according to claim 2, wherein $R^6$ is an optionally substituted $C_{1-6}$ alkyl group or an optionally substituted $C_{3-10}$ cycloalkyl group.

7. The method according to claim 2, wherein $R^6$ is a $C_{1-6}$ alkyl group, a $C_{3-10}$ cycloalkyl group, a $C_{3-10}$ cycloalkyl-$C_{1-6}$ alkyl group, or a mono- or di-$C_{6-10}$ aryl-$C_{1-6}$ alkyl group.

8. The method according to claim 2, wherein both $R^a$ and $R^b$ are hydrogen atoms.

9. The method according to claim 2, wherein said compound represented by the formula (I) or a salt thereof is a compound selected from the group consisting of
1-benzyl-3-(3-cyanophenyl)thiourea;
1-benzyl-3-[4-(trifluoromethyl)phenyl]thiourea;
1-benzyl-3-(4-bromophenyl)thiourea;
1-(4-cyanophenyl)-3-cyclooctyl-thiourea;
1-(4-cyanophenyl)-3-cyclohexyl-thiourea;
1-(4-cyanophenyl)-3-(cyclohexylmethyl)thiourea;
1-benzhydryl-3-(4-cyanophenyl)thiourea; and
1-butyl-3-(4-cyanophenyl)thiourea,
or a salt of said compound.

10. A method for antagonizing a sweetness receptor, which comprises administering to a subject in need thereof a compound represented by formula (I):

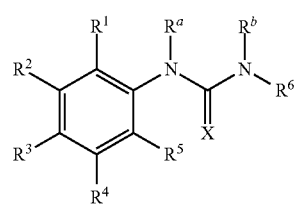

wherein
$R^1$, $R^2$, $R^3$, $R^4$, and $R^5$ are each independently a hydrogen atom or an electron-withdrawing group, provided at least one of $R^1$, $R^2$, $R^3$, $R^4$, and $R^5$ is an electron-withdrawing group;
$R^6$ is an optionally substituted hydrocarbon group or an optionally substituted heterocyclic group;
$R^a$ and $R^b$ are each independently a hydrogen atom or a $C_{1-6}$ alkyl group; and
X is S,
or a salt thereof.

11. A method for sensitizing insulin, which comprises administering to a subject in need thereof a compound represented by formula (I):

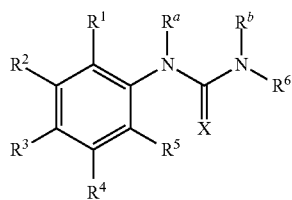

(I)

wherein
$R^1$, $R^2$, $R^3$, $R^4$, and $R^5$ are each independently a hydrogen atom or an electron-withdrawing group, provided at least one of $R^1$, $R^2$, $R^3$, $R^4$, and $R^5$ is an electron-withdrawing group;
$R^6$ is an optionally substituted hydrocarbon group or an optionally substituted heterocyclic group;
$R^a$ and $R^b$ are each independently a hydrogen atom or a $C_{1-6}$ alkyl group; and
X is S,
or a salt thereof.

12. The method according to claim 10, wherein $R^6$ is a $C_{1-6}$ alkyl group, a $C_{3-10}$ cycloalkyl group, a $C_{3-10}$ cycloalkyl-$C_{1-6}$ alkyl group, or a mono- or di-$C_{6-10}$ aryl-$C_{1-6}$ alkyl group.

13. The method according to claim 10, wherein both $R^a$ and $R^b$ are hydrogen atoms.

14. The method according to claim 10, wherein said compound represented by the formula (I) or a salt thereof is a compound selected from the group consisting of
1-benzyl-3-(3-cyanophenyl)thiourea;
1-benzyl-3-[4-(trifluoromethyl)phenyl]thiourea;
1-benzyl-3-(4-bromophenyl)thiourea;
1-(4-cyanophenyl)-3-cyclooctyl-thiourea;
1-(4-cyanophenyl)-3-cyclohexyl-thiourea;
1-(4-cyanophenyl)-3-(cyclohexylmethyl)thiourea;
1-benzhydryl-3-(4-cyanophenyl)thiourea; and
1-butyl-3-(4-cyanophenyl)thiourea,
or a salt of said compound.

15. The method according to claim 11, wherein $R^6$ is a $C_{1-6}$ alkyl group, a $C_{3-10}$ cycloalkyl group, a $C_{3-10}$ cycloalkyl-$C_{1-6}$ alkyl group, or a mono- or di-$C_{6-10}$ aryl-$C_{1-6}$ alkyl group.

16. The method according to claim 11, wherein both $R^a$ and $R^b$ are hydrogen atoms.

17. The method according to claim 11, wherein said compound represented by the formula (I) or a salt thereof is a compound selected from the group consisting of
1-benzyl-3-(3-cyanophenyl)thiourea;
1-benzyl-3-[4-(trifluoromethyl)phenyl]thiourea;
1-benzyl-3-(4-bromophenyl)thiourea;
1-(4-cyanophenyl)-3-cyclooctyl-thiourea;
1-(4-cyanophenyl)-3-cyclohexyl-thiourea;
1-(4-cyanophenyl)-3-(cyclohexylmethyl)thiourea;
1-benzhydryl-3-(4-cyanophenyl)thiourea; and
1-butyl-3-(4-cyanophenyl)thiourea,
or a salt of said compound.

* * * * *